(12) United States Patent
Crawford et al.

(10) Patent No.: US 11,937,871 B2
(45) Date of Patent: Mar. 26, 2024

(54) DEVICES, SYSTEMS, AND METHODS FOR ACCESSING A BODY LUMEN

(71) Applicant: Boston Scientific Scimed, Inc., Maple Grove, MN (US)

(72) Inventors: Richard Crawford, Galway (IE); Louis McNern, Donegal (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 16/930,764

(22) Filed: Jul. 16, 2020

(65) Prior Publication Data
US 2021/0015548 A1    Jan. 21, 2021

Related U.S. Application Data

(60) Provisional application No. 62/875,292, filed on Jul. 17, 2019.

(51) Int. Cl.
*A61B 18/14* (2006.01)
*A61B 18/00* (2006.01)
*A61B 18/12* (2006.01)

(52) U.S. Cl.
CPC ...... *A61B 18/1487* (2013.01); *A61B 18/1206* (2013.01); *A61B 18/1492* (2013.01);
(Continued)

(58) Field of Classification Search
CPC .. A61B 2018/0016; A61B 2018/00166; A61B 2018/00267; A61B 2018/144; A61B 2018/1465; A61B 2018/1475; A61B 2018/00077; A61B 2018/00702; A61B 2018/0091; A61B 2018/00982;
(Continued)

(56) References Cited

U.S. PATENT DOCUMENTS 4,699,147 A * 10/1987 Chilson ............... A61B 5/6858
                                                          600/374
6,676,659 B2    1/2004 Hutchins et al.
(Continued)

OTHER PUBLICATIONS

International Search Report and Written Opinion for the International Patent Application No. PCT/US2020/042291, dated Sep. 30, 2020, 11 pages.

*Primary Examiner* — Khadijeh A Vahdat
*Assistant Examiner* — Marina Delaney Templeton
(74) *Attorney, Agent, or Firm* — Seager, Tufte & Wickhem LLP

(57) ABSTRACT

The present disclosure relates generally to the field of medical devices for accessing body lumens. In particular, the present disclosure relates to medical devices, systems and methods for enlarging an opening of a body lumen. In an embodiment, a device may include a flexible elongate tube. A distal end of the tube may be configured to access an opening of a body lumen. A plurality of wire lumens may extend from the distal end of the tube toward a proximal end of the tube that are radially offset from and substantially parallel with a longitudinal axis. At least a portion of the plurality of wire lumens may be exposed to an outer surface of the tube along a distal portion. A plurality of wires may each extend along a respective wire lumen. A portion of each wire may extend externally to the wire lumens exposed to the outer surface.

20 Claims, 11 Drawing Sheets

(52) U.S. Cl.
CPC ........... *A61B 2018/00077* (2013.01); *A61B 2018/00601* (2013.01); *A61B 2018/00702* (2013.01); *A61B 2018/0091* (2013.01); *A61B 2018/00982* (2013.01); *A61B 2018/1253* (2013.01); *A61B 2018/126* (2013.01)

(58) Field of Classification Search
CPC ........... A61B 18/1487; A61B 18/1206; A61B 18/1492; A61M 25/0147; A61M 25/0074
See application file for complete search history.

(56) References Cited

U.S. PATENT DOCUMENTS

| | | | |
|---|---|---|---|
| 6,827,718 B2 | 12/2004 | Hutchins et al. | |
| 7,200,445 B1* | 4/2007 | Dalbec | A61B 18/1492 606/41 |
| 7,371,237 B2 | 5/2008 | Hutchins et al. | |
| 7,635,363 B2 | 12/2009 | Hutchins et al. | |
| 8,231,621 B2 | 7/2012 | Hutchins et al. | |
| 8,579,895 B2 | 11/2013 | Hutchins et al. | |
| 9,352,124 B2 | 5/2016 | Hutchins et al. | |
| 10,569,050 B1* | 2/2020 | Heesch | A61M 25/0074 |
| 2003/0208219 A1 | 11/2003 | Aznoian et al. | |
| 2007/0093803 A1* | 4/2007 | Dalbec | A61B 18/1492 606/41 |
| 2007/0282358 A1* | 12/2007 | Remiszewski | A61B 1/0057 606/159 |
| 2014/0128844 A1 | 5/2014 | Kornowski et al. | |
| 2014/0188103 A1* | 7/2014 | Millett | A61B 18/1492 606/34 |
| 2014/0276752 A1* | 9/2014 | Wang | A61B 18/1492 606/41 |
| 2016/0256217 A1 | 9/2016 | Hutchins et al. | |
| 2016/0338771 A1* | 11/2016 | Kobayashi | A61B 18/1492 |
| 2017/0071544 A1* | 3/2017 | Basu | A61B 5/333 |
| 2019/0201689 A1* | 7/2019 | Teng | A61N 1/36002 |
| 2020/0038166 A1 | 2/2020 | Kim | |
| 2020/0214764 A1 | 7/2020 | Wilder et al. | |

* cited by examiner

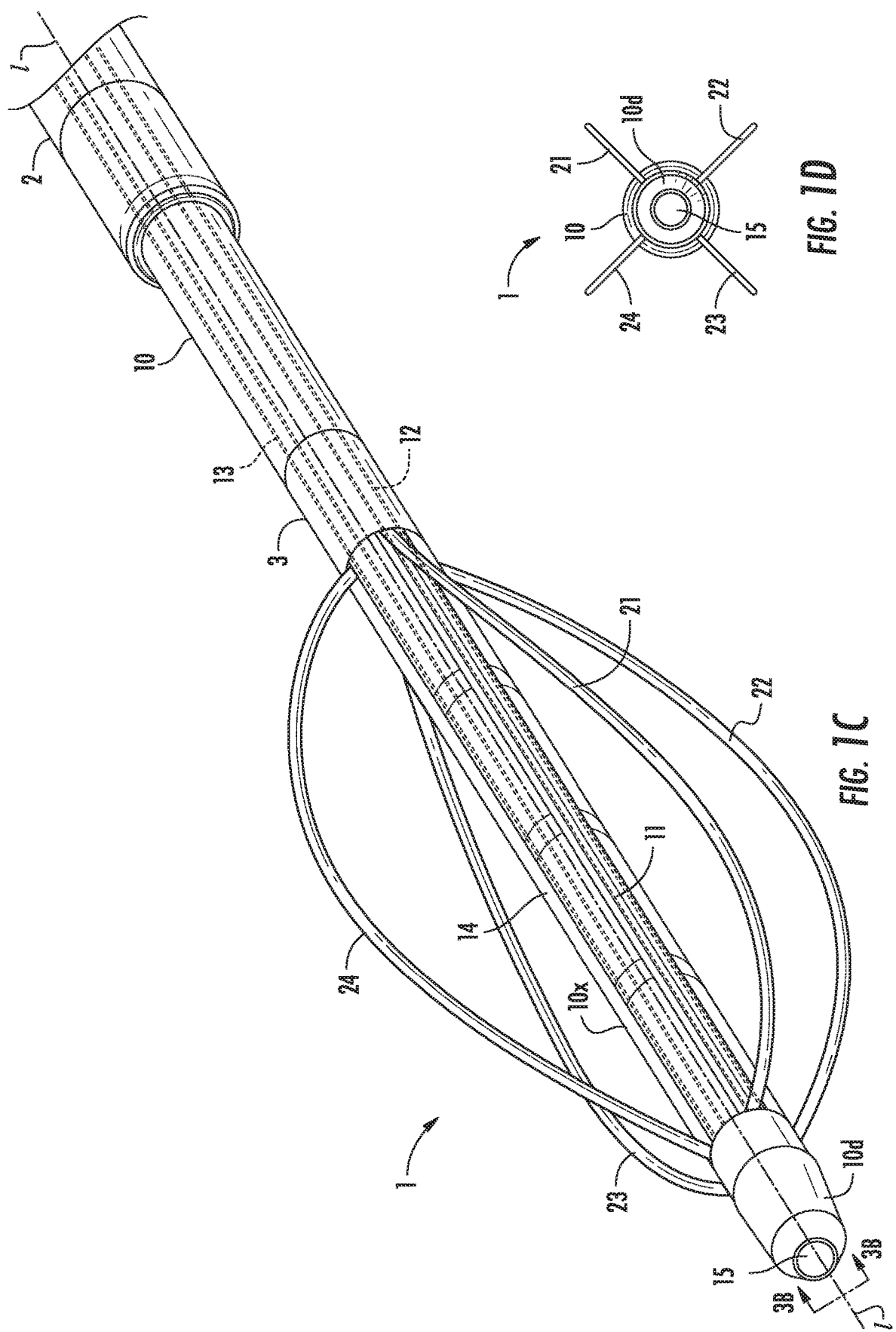

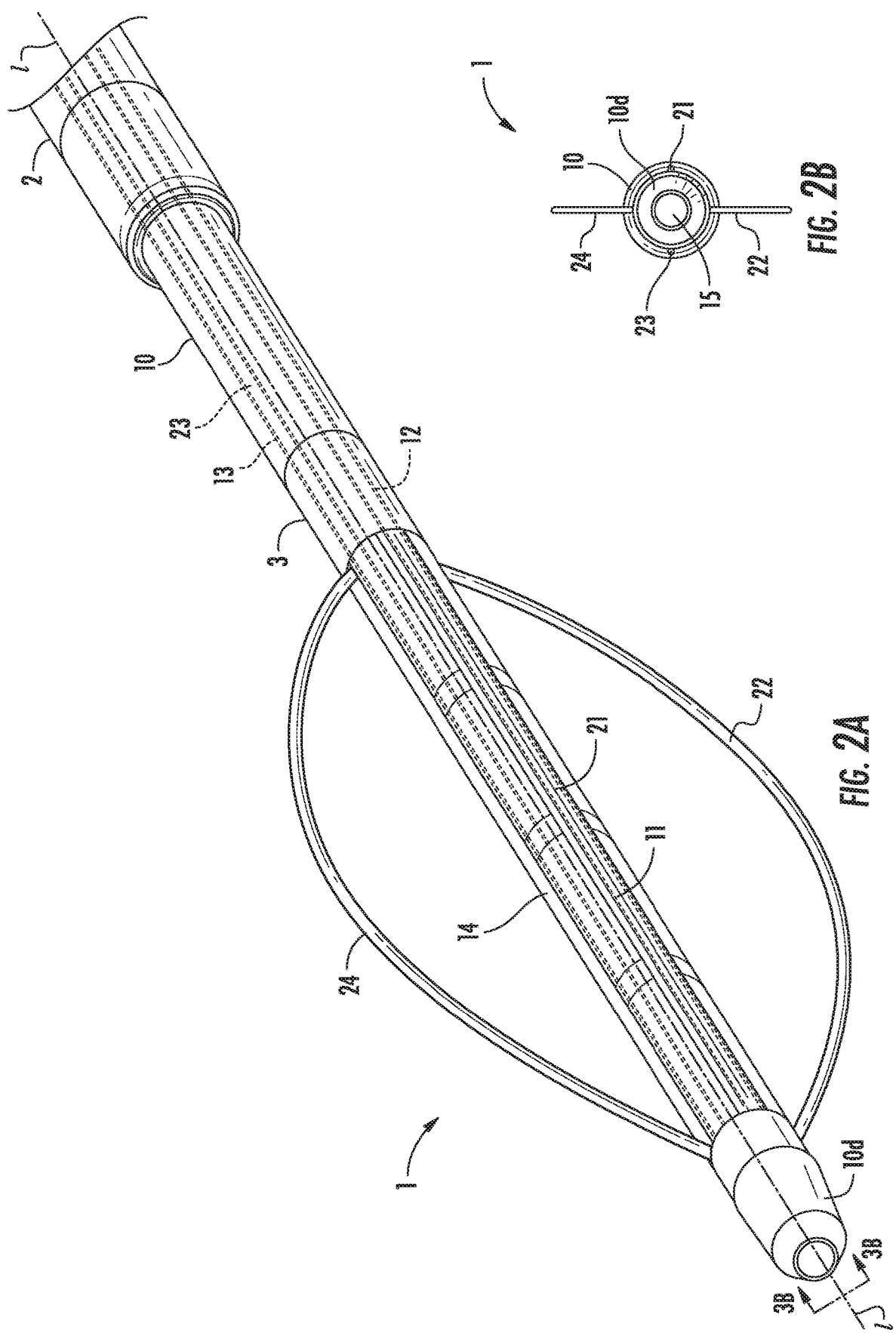

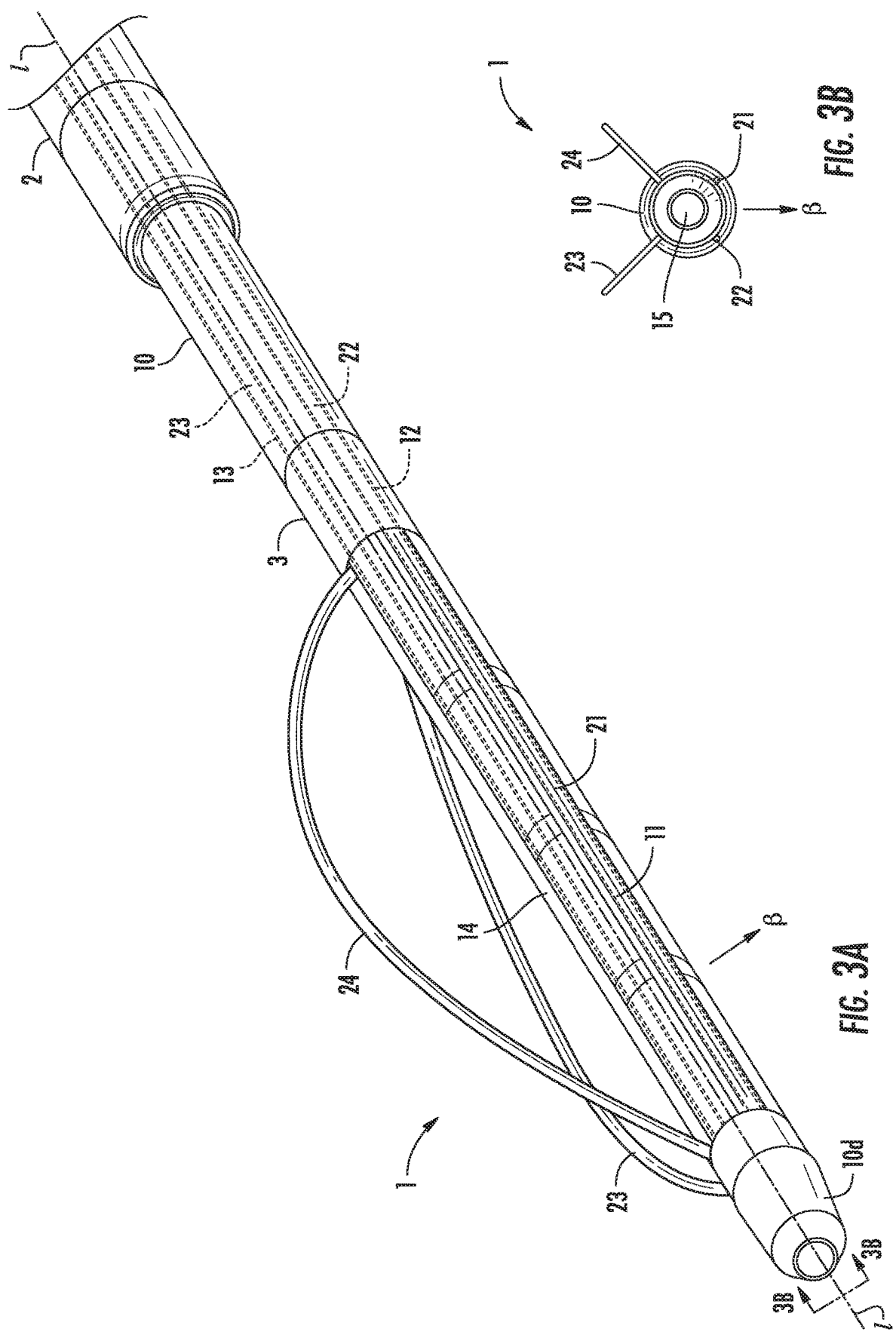

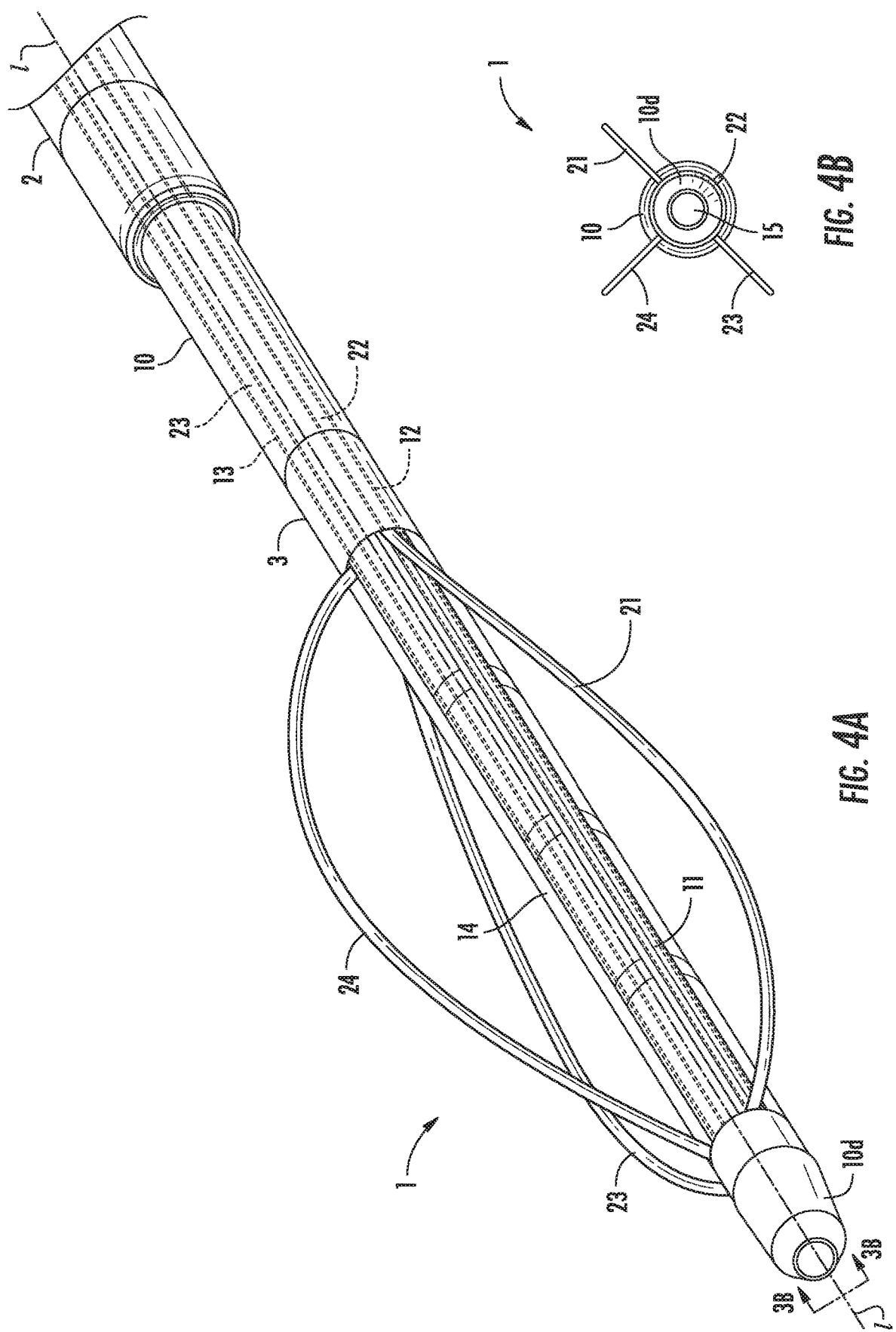

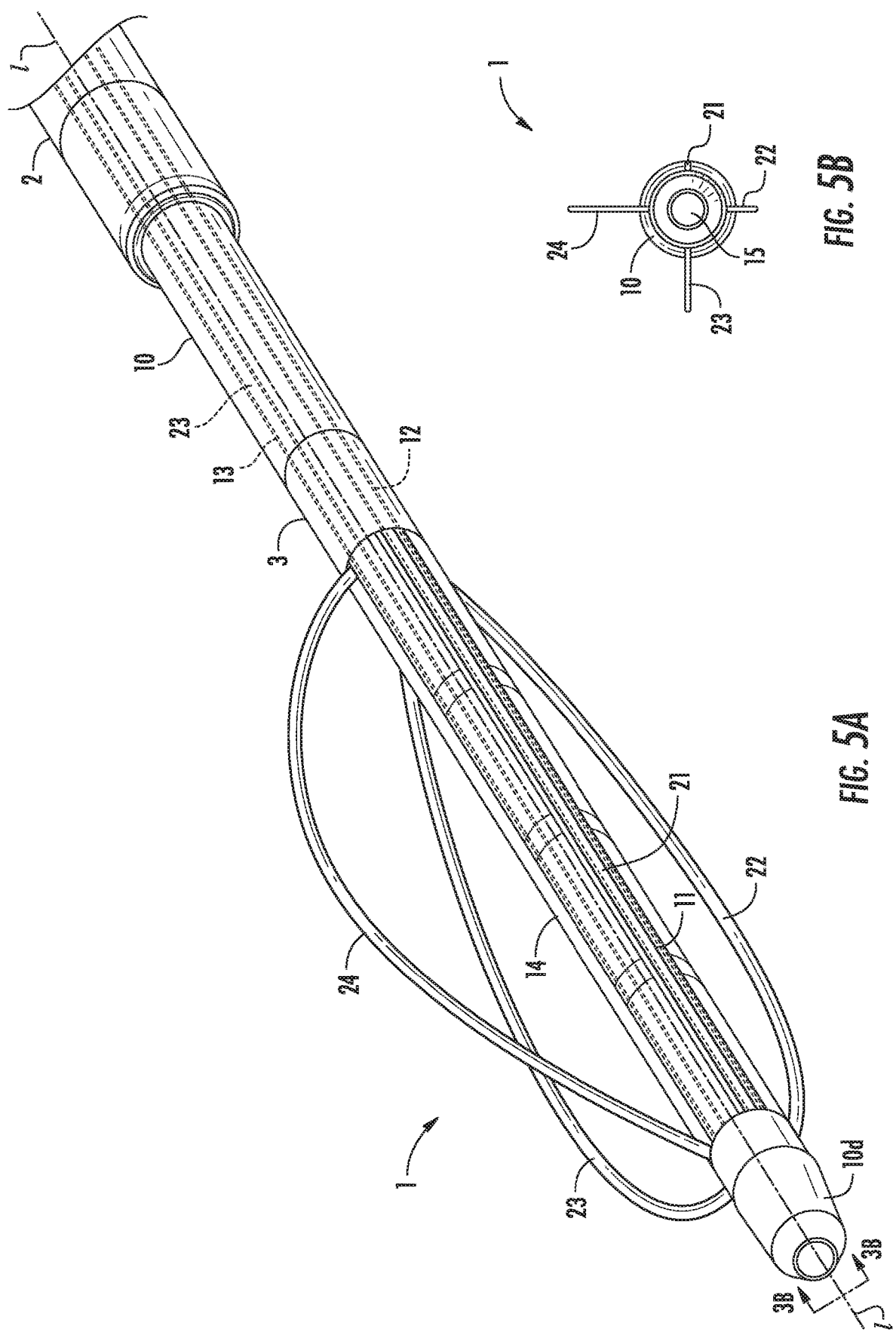

DEVICES, SYSTEMS, AND METHODS FOR ACCESSING A BODY LUMEN

PRIORITY

This application claims the benefit of priority under 35 USC § 119 to U.S. Provisional Patent Application Ser. No. 62/875,292, filed Jul. 17, 2019, which is incorporated by reference herein in its entirety and for all purposes.

FIELD

The present disclosure relates generally to the field of medical devices for accessing a body lumen. In particular, the present disclosure relates to medical devices, systems and methods for targeted access to and enlarging of a body lumen opening.

BACKGROUND

Medical professionals sometimes face significant technical challenges when accessing a body lumen, such as when performing endoscopic cannulation procedures that may involve advancing a guidewire and/or endoscopic device (e.g., sphincterotome, cannula, catheter, or the like) against, into, or through tortuous patient anatomies.

For example, a target body lumen, e.g., biliary sphincter, may be oriented at a difficult angle relative to the endoscopic device, have a very small or sealed opening, or include a tortuous anatomy, or blockages formed, e.g., stones, or benign or malignant strictures. Precise control of movement and force of the device and guidewire can be challenging. Even experienced medical professionals may make multiple attempts to achieve successful opening and access to body lumens, especially when working against the friction and patient-specific pathologies of a specific body lumen. The likelihood of causing trauma to tissues comprising or surrounding a target body passageway increases with the number of opening or entry attempts. In some instances, the medical professional may abort the procedure entirely. In other instances, traumatized tissue may be prone to post-operative inflammation. Even after cannulation, further device manipulation may be required to orient a cutting portion of the device toward a target tissue.

It is with these considerations in mind that the improvements of the present disclosure may be useful.

SUMMARY

Embodiments of the present disclosure may assist generally with accessing and/or enlarging an opening of a body lumen without the need to exchange multiple devices and/or use devices that do not optimize maneuverability and controlled enlarging and/or cutting. In one aspect of the present disclosure, a medical device may include a flexible elongate tube having a proximal end, a distal end, a longitudinal axis extending along a length of the tube, an outer surface, and a distal portion proximal to the distal end. The distal end may be configured to access an opening of a body lumen. A plurality of wire lumens may extend from the distal end of the tube toward the proximal end of the tube. The wire lumens may be radially offset from and substantially parallel with the longitudinal axis. At least a portion of each of the plurality of wire lumens may be exposed to the outer surface along the distal portion. A central lumen may extend from the distal end of the tube toward the proximal end of the tube. The medical device may have a plurality of wires. Each wire may extend along a respective wire lumen. A portion of each wire may be extendable externally to the respective wire lumen along the portion of the wire lumen exposed to the outer surface. A sheath may be slidable about the flexible elongate tube.

In various embodiments described here and otherwise, a medical device may include a shoulder disposed on the distal end of the flexible elongate tube. The shoulder may have an outer diameter that is at least as wide as an inner diameter of the sheath. At least one of the plurality of wires may be electrically conductive and configured to be coupled to a power source. Each of the plurality of wires may be configured to articulate the distal end of the flexible elongate tube when the wire is translated proximally through the respective wire lumen. Each of the plurality of wires may be individually transitionable between an undeployed configuration substantially within the respective wire lumen, and a deployed configuration with a portion of the wire extended radially away from the respective wire lumen. A handle may be at the proximal end of the flexible elongate tube. The handle may include a pulley assembly connected to each of the plurality of wires. The handle may be actuatable to individually translate the wires within the respective wire lumens. Each of the plurality of wire lumens may be arranged circumferentially about the longitudinal axis. Each of the plurality of wires may be visually marked such that they are differentiated from at least one other wire of the plurality of wires.

In an aspect, a medical device may include a flexible elongate tube having a proximal end, a distal end, a longitudinal axis extending along a length of the tube, an outer surface, and a distal portion proximal to the distal end. The distal end may be configured to access an opening of a body lumen. A distal band may be disposed about the flexible elongate tube at the distal end. A plurality of wire lumens may extend from the distal end of the tube toward the proximal end of the tube. The wire lumens may be radially offset from and substantially parallel with the longitudinal axis. At least a portion of each of the plurality of wire lumens may be open along the outer surface along the distal portion. A central lumen may extend from the distal tip toward the proximal end of the tube. The medical device may include a plurality of wires. Each wire may extend along a respective wire lumen. A portion of each wire may be configured to extend externally to the respective wire lumen along the portion of the wire lumen open along the outer surface.

In various embodiments, a sheath may be slidable about a flexible elongate tube. The sheath may have a sheath band disposed about the sheath at a distal end of the sheath. A distal band and the sheath band may be visually marked such that they are differentiated from each other. The sheath band may distally taper from a larger diameter to a smaller diameter. A handle may be at the proximal end of the flexible elongate tube. The handle may include a pulley assembly connected to each of a plurality of wires, wherein the handle is actuatable to independently slide each of the plurality of wires within respective wire lumens. A handle may be at the proximal end of the flexible elongate tube. The handle may include the pulley assembly connected to each of the plurality of wires. The handle may be actuatable to selectively slide each of the plurality of wires within the respective wire lumens.

In an aspect, a method of accessing an opening of a body lumen may include inserting a flexible elongate tube of a medical device having a distal end into a patient to the opening of the body lumen. The distal end of the elongate tube may be articulated toward the opening of the body lumen via at least one of a plurality of conductive wires extending within respective lumens through the flexible elongate tube. The plurality of wires may be connected at the distal end of the tube. Each of the plurality of wires may have a distal portion extendable radially from the respective lumen external to an outer surface of the elongate tube. A first wire of the plurality of wires may extend radially outward to a first radial distance from the elongate tube into contact with the body lumen. At least one of the plurality of wires may be energized.

In some embodiments, a distal end of the elongate tube may be articulated by sliding one or more of the plurality of wires proximally relative to the tube. An opening of the body lumen may be cannulated with the distal end of the elongate tube. A second wire of the plurality of wires may extend radially outward to a second radial distance from the elongate tube into contact with the body lumen. A sheath may be retracted from about the flexible elongate tube after cannulating the opening of the body lumen. Multiple wires of the plurality of wires may be extended radially outward to the first radial distance from the elongate tube into contact with the body lumen. Multiple wires of the plurality of wires may be extended radially outward to a second radial distance from the elongate tube into contact with the body lumen. A guidewire may be extended through a central lumen of the elongate tube into the body lumen. A first wire of the plurality of wires may be extended radially outward. A second wire may be sequentially extended outward. At least one of the wires may be selectively energized. The distal end of the tube may be articulated using at least one of the plurality of wires that is a different wire than the at least one wire of the plurality of wires that is energized.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1C illustrates an isometric view of the device of FIGS. 1A and 1B with the wires deployed.

FIG. 1D illustrates a front view of FIG. 1C.

FIG. 2A illustrates an isometric view of the device of FIGS. 1A-1D with two wires deployed in a single plane.

FIG. 2B illustrates a front view of FIG. 2A.

FIG. 3A illustrates an isometric view of the device of FIGS. 1A-2B with two wires deployed perpendicularly from each other.

FIG. 3B illustrates a front view of FIG. 3A.

FIG. 4A illustrates an isometric view of the device of FIGS. 1A-3B with three wires deployed.

FIG. 4B illustrates a front view of FIG. 4A.

FIG. 5A illustrates an isometric view of the device of FIGS. 1A-4B with three wires deployed at various radial distances from the device.

FIG. 5B illustrates a front view of FIG. 5A.

DETAILED DESCRIPTION

Figure 1A:
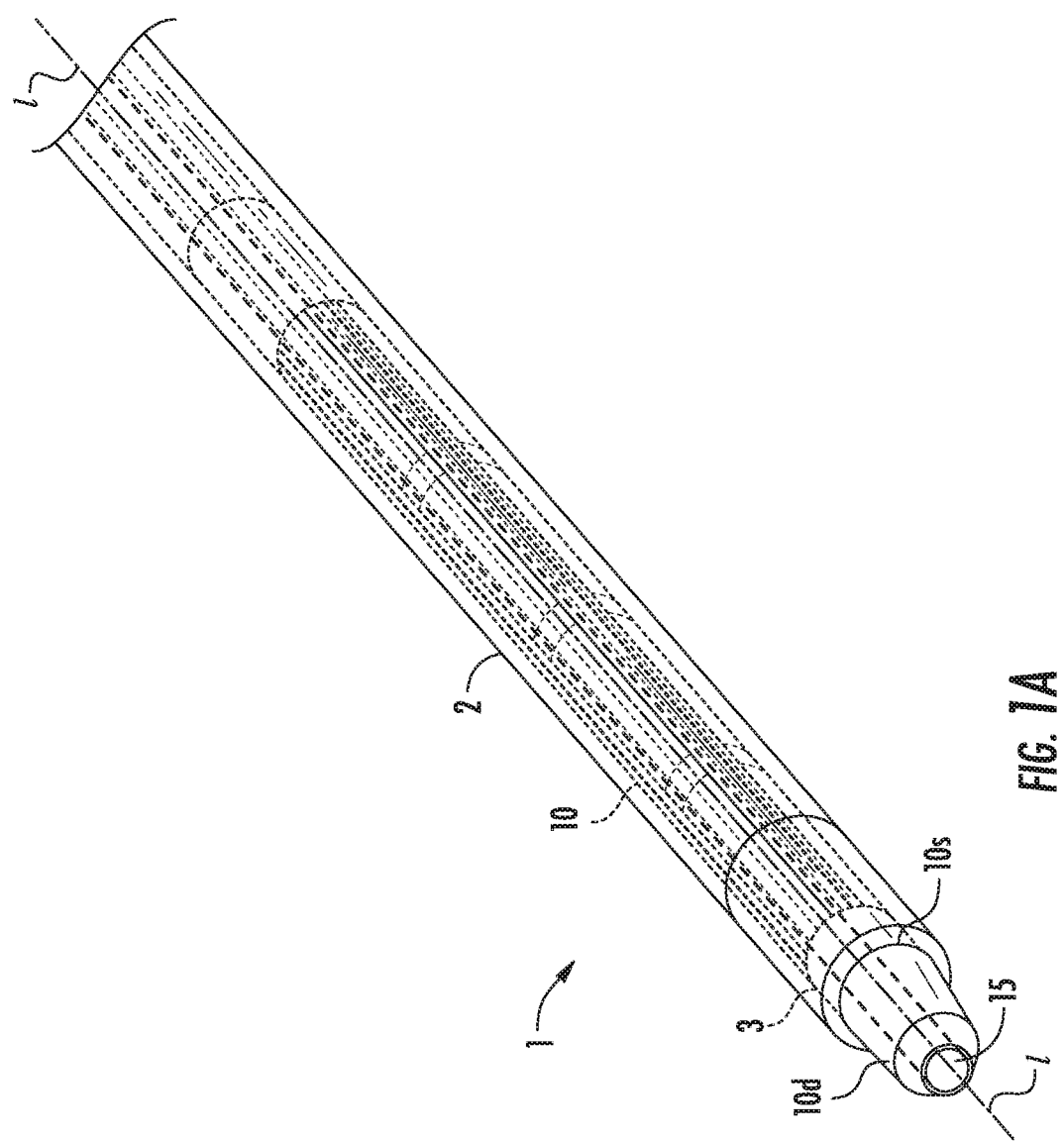
FIG. 1A illustrates an isometric view of a device having wires covered by a sheath in a closed configuration, according to an embodiment of the present disclosure.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., endoscopic devices, accessory tools, and/or guidewires inserted through a duodenoscope, near or through a papilla, or the like) for selective access to, aligning with, cannulation, enlarging, and/or cutting of the opening to the common bile duct (CBD) or pancreatic duct (PD) during endoscopic retrograde cholangiopancreatography (ERCP), it should be appreciated that such medical devices and systems may be used in a variety of medical procedures for navigating one or more devices through ductal, luminal, vascular, or body lumen anatomies, including, for example, interventional radiology procedures, balloon angioplasty/angiography procedures, thrombolysis procedures, urological or gynecological procedures, and the like. The medical devices herein are also not limited to use with duodenoscopes and may include a variety of medical devices for accessing body passageways, including, for example, catheters, ureteroscopes, bronchoscopes, colonoscopes, arthroscopes, cystoscopes, hysteroscopes, and the like. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

To facilitate smooth and efficient entry of a guidewire and an endoscopic device into/through a target body lumen, medical professionals may manually rotate, oscillate, linearly advance, and/or reciprocate the endoscopic device and guidewire to "wiggle" against, into, or through the body lumen. For example, endoscopic retrograde cholangiopancreatography (ERCP) may be performed by trained gastroenterologists and surgical endoscopists to diagnose and treat various disorders of the pancreaticobiliary system. Physicians in such procedures may use a sphincterotome to cannulate a body lumen (e.g., the papillary orifice or the like). A sphincterotome may include a guidewire, so that after initial cannulation the guidewire can be inserted into the biliary duct. A sphincterotome may include a cutting wire for enlarging/cutting/accessing tissue to enlarge an opening for access (e.g., a sphincterotomy or the like). A sphincterotome may have a flexible distal end that may be articulated (e.g., steered, bowed, manipulated, or the like) by articulating a cutting wire of the device. The distal end of the sphincterotome may need to be extended into the opening of the body lumen, so that the cutting wire may extend to the tissue of the opening for enlarging or cutting. The target tissue to be treated may be located further within the body lumen, past the point of initial cannulation, so that the device is further steered through the body lumen to the target tissue.

Figure 1B:
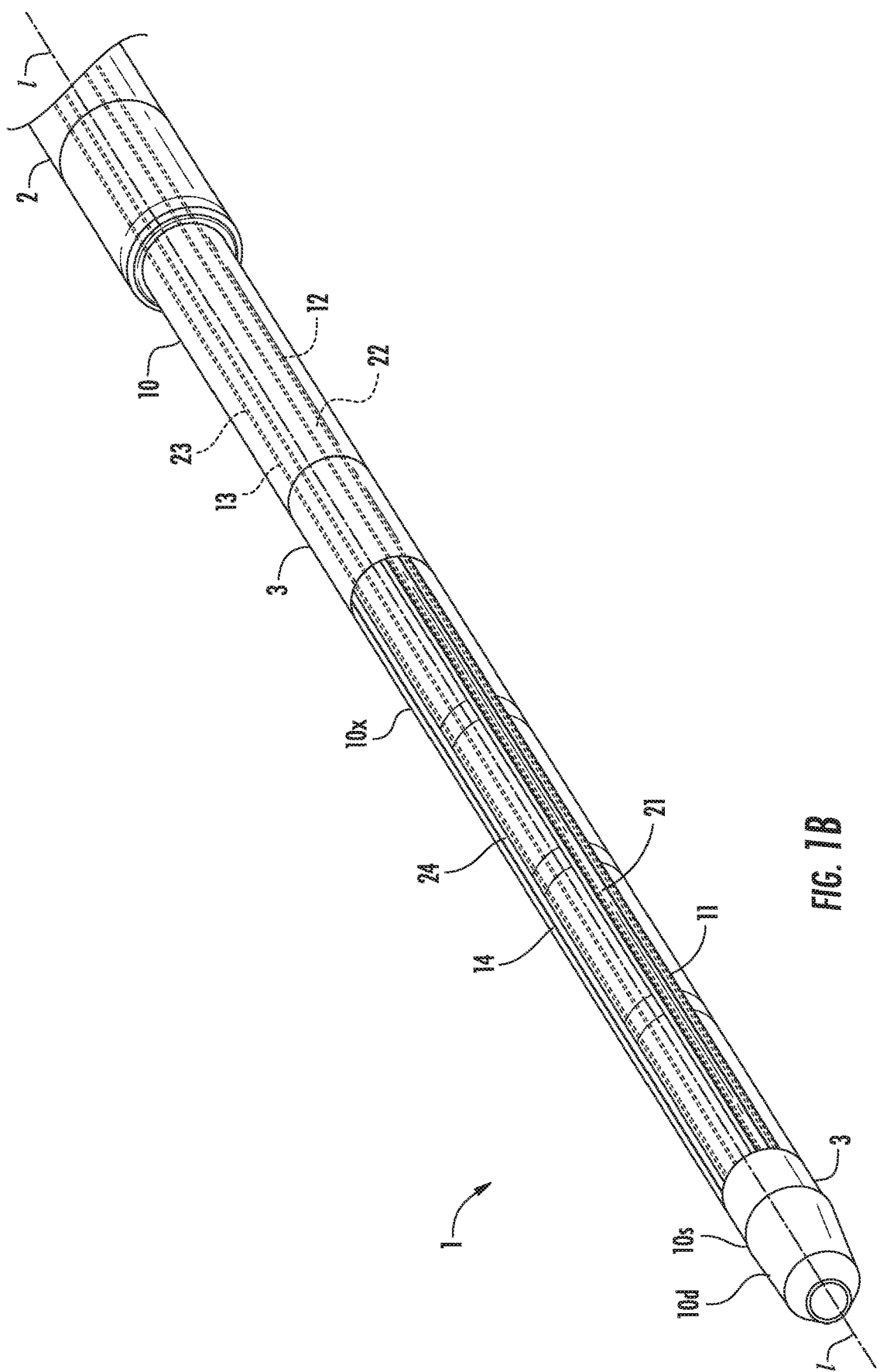
FIG. 1B illustrates an isometric view of the device of FIG. 1A with the wires exposed in an open configuration.

With reference to FIGS. 1A and 1B, an embodiment of a device 1 for accessing a body lumen according to the present disclosure is illustrated, which includes a flexible elongate tube 10 having a proximal end, a distal end 10d, a longitudinal axis l extending from the proximal end along a length of the tube 10 to the distal end 10d. Four wire lumens 11, 12, 13, 14 extend from the distal end 10d of the tube toward the proximal end of the tube 10 and are arranged circumferentially about the longitudinal axis l. Although four wire lumens 11, 12, 13, 14 are depicted, in some embodiments a tube 10 may have fewer or additional wire lumens, e.g., 1, 2, 3, 5, 6, 7, 8, 10, etc. The wire lumens 11, 12, 13, 14 are radially offset from and are substantially parallel with the longitudinal axis l. A portion of the wire lumens 11, 12, 13, 14 are radially exposed to an outer surface of the tube 10 along a distal portion 10x of the tube 10. A central lumen 15 extends from the distal end 10d of the tube 10 toward the proximal end of the tube 10. The central lumen 15 may accept a medical instrument (e.g., a guidewire) or a fluid (e.g., a contrast agent). The distal end 10d tapers from a larger diameter to a smaller diameter in a distal direction along the longitudinal axis l (e.g., in a conical, or frusto-conical shape) so that a smaller leading diameter may be used to enter a body lumen. The distal end 10d may have a distal tip that is rounded and/or otherwise blunted for atraumatic entry, e.g., into body lumens. Four wires 21, 22, 23, 24 each extend along a respective wire lumen 11, 12, 13, 14. Each wire 21, 22, 23, 24 is connected to the distal end 10d of the elongate tube 10. A portion of each wire 21, 22, 23, 24 along the distal portion 10x of the tube 10 extends partially external from the respective lumens 11, 12, 13, 14 to the elongate tube 10. The wires 21, 22, 23, 24 are exposed to and substantially flush with the outer surface of the tube 10 at the distal portion 10d. Although the wires 21, 22, 23, 24 are flush with the outer surface of the tube 10, in some embodiments, the wires 21, 22, 23, 24 may be less than flush with the surface of the tube 10 within the lumens 11, 12, 13, 14 (i.e., the wires 21, 22, 23, 24 are below the surface of the tube 10) or the wires 21, 22, 23, 24 may extend radially from the surface of the tube 10 (i.e., the wires 21, 22, 23, 24 extend outside the surface of the tube 10 such that the wires 21, 22, 23, 24 extend past a portion of the circumference of the lumen beyond the surface of the tube 10). The wires 21, 22, 23, 24 may be articulatable with respect to the wire lumens 11, 12, 13, 14 in an exposed or in an unexposed configuration. In some embodiments, each wire 21, 22, 23, 24 may be individually disposed in a respective lumen 11, 12, 13, 14. In some embodiments, one or more lumens 11, 12, 13, 14 may be sized to receive more than a single wire 21, 22, 23, 24, e.g., a lumen 11 may be sized to receive wires 21 and 22. Wires 21, 22, 23, 24 may be conductive or insulative, or partially conductive and partially insulative. It is also understood that additional or fewer wires may be included in the device 1 to match the number of lumens, e.g., 1, 2, 3, 5, 6, 7, 8, 10, etc.

A sheath 2 is slidable axially and rotationally about the flexible elongate tube 10. In FIG. 1A, the sheath 2 is extended over the tube 10 to the distal end 10d such that the sheath 2 encloses or covers the wires 21, 22, 23, 24 in a closed configuration. The distal end 10d of the tube 10 includes a shoulder 10s having an outer diameter that is wider than an inner diameter of the sheath 2 such that the sheath 2 cannot be extended distally past the shoulder 10s. In FIG. 1B, the sheath 2 is retracted proximally away from the distal portion 10x of the tube 10 such that a portion of the wires 21, 22, 23, 24 are exposed at the distal portion 10x in an open configuration. Marker bands 3 are disposed about various portions of the device 1 to visually indicate to a medical professional the location and orientation of the device 1. One or more of the marker bands 3 may be visually inspected by the medical professional in relation to other marker bands 3 and/or anatomy to indicate the position of the portion of the device with the marker band 3. The marker bands 3 may be various colors and/or various radiopacity such that the marker bands can be differentiated from each other, various locations on the device 1 can be identified, and distances in the patient's anatomy can be measured by using the marker bands 3. Marker bands 3 are located on the distal portion of the sheath 2, on the tube 10 proximal to the distal portion 10x, on the tube 10 along the distal portion 10x, and on the distal end 10d, although marker bands 3 may be disposed anywhere along the device 1 where a medical professional may desire to visually locate the device in the patient's anatomy.

In various embodiments, one or more wires may be conductive and coupled to a power source in order to deliver energy to the wires. The wires may be insulated along at least a portion of a length of the wires and/or the wires may be non-insulated along at least a portion of the length of the wires. Electrically conductive wires may be part of an electrical circuit that is monopolar or bipolar and may be selectively activated such that one or more wires are energized while one or more other wires are not energized.

A bipolar circuit may have the cutting wire coupled to and/or in electrical communication with a radio frequency (RF) generator, such as an electrosurgical unit. When the RF generator is activated, the RF generator may supply electrical current to the selected wire(s), which may cut the sphincter muscle to enlarge the opening. The electrical current may travel along the wire, through the target tissue (e.g., sphincter muscle), and then along a return path, which completes the circuit. The return path may be one or more additional wires.

A monopolar circuit may include a current return path including a neutral electrode, which may be positioned externally to the patient (e.g., on the thigh of the patient). The distal portion of the elongate tube and/or the distal end of one or more wires may be configured to deliver real-time feedback information (e.g., an electrical resistance, tissue temperature and/or impedance, a force of the device against a tissue, an activation time, a current, etc.) to a medical professional or computer processor, to manually or automatically adjust, e.g., increase or decrease, the frequency, power, and/or duration of energy being delivered.

In various embodiments, a distal end of a device may be a separate member that is coupled to the distal end of a flexible elongate tube. The distal end may include a proximally extending rod or tubular member that may be coupled to the distal end of the flexible elongate tube. For example, the distal end of a device may be partially inserted and/or bonded to a central lumen of the flexible elongate tube. As another example, a connector ring may be disclosed on the distal end of the tube and the distal end of the device may be connected to the connector ring. The distal end of a device may comprise a similar, substantially similar, or different material than the tube such as polyether ether ketone (PEEK), polytetrafluoroethylene (PTFE), fluorinated ethylene propylene (FEP), a combination thereof, or the like. Wires of a device may be coupled to and/or within the distal end of a device and/or may be coupled to a distal end of a tube. For example, the wires may be separately isolated from each other and bonded within the distal end of the device or within a distal end of a tube.

With reference to FIGS. 1C and 1D, the wires 21, 22, 23, 24 of the device 1 are deployed along the distal portion 10x of the flexible elongate tube 10. The wires 21, 22, 23, 24 are deployed out of the wire lumens 11, 12, 13, 14 radially away from the longitudinal axis l by a medical professional distally translating the wires 21, 22, 23, 24 through the lumens 11, 12, 13, 14 while the device 1 is in the open configuration with the sheath 2 slid proximally. The wires 21, 22, 23, 24 are deployed such that they may extend to contact a target tissue of a body lumen that may be remote from the longitudinal axis l. The wires 21, 22, 23, 24 may be deployed such that a point of each wire 21, 22, 23, 24 extended farthest from the tube 10 are each at equal distances radially away from the longitudinal axis l to assist in centering the device 1, or to assist in centering the central lumen 15, or to assist in maintaining body lumen patency, e.g., in the configuration illustrated in FIGS. 1C and 1D. If a target tissue is close to the outer surface of the tube 10, the wires 21, 22, 23, 24 may not need to be deployed and may be selectively energized without deployment, e.g., in the configuration illustrated in FIG. 1B with the sheath 2 retracted proximally such that the wires 21, 22, 23, 24 are exposed to make a diathermy connection.

With reference to FIGS. 2A and 2B, an embodiment of the device is depicted with the wires 21, 22, 23, 24 of the device 1 selectively deployed such that two of the wires 22, 24 are deployed and two of the wires 21, 23 are not deployed. The two deployed wires 22, 24 may be two opposing wires 22, 24 that extend radially away from the longitudinal axis l in a plane that extends parallel to the longitudinal axis l. Additionally, or in the alternative, two of the wires 23, 24 of the device 1 may be selectively deployed such that the two wires 23, 24, are deployed and two of the wires 21, 22 are not deployed, as illustrated in FIGS. 3A and 3B. The two deployed wires 23, 24 may be offset from each other at an angle α about the longitudinal axis l that may be, e.g., substantially perpendicular (about 90°). The two deployed wires 23, 24 may be energized in a monopolar or bipolar fashion and/or may assist in moving/orienting the device 1 in the direction β opposing the deployed wires 23, 24 such that the two undeployed wires 21, 22 may make contact with a target tissue for treatment. Additionally, or in the alternative, three of the wires 22, 23, 24 of the device 1 may be selectively deployed such that the three wires 22, 23, 24, are deployed and the remaining wire 21 is not deployed, as illustrated in FIGS. 4A and 4B. The three deployed wires 22, 23, 24 may be selectively energized in a monopolar or bipolar fashion and/or may assist in moving/orienting the device 1 in the radial direction of the undeployed wire 21. It is understood that any of the wires 21, 22, 23, 24 may be independently deployed and/or energized from each other. For example, wire 21 may be deployed to a first distance and energized, wire 22 may be deployed but not energized, wire 23 may be undeployed and not energized, and wire 24 may be deployed to a second distance and energized, etc. The wires 21, 22, 23, 24 may form any combination of deployment, distance from the tube 10, and energization as desired by the medical professional.

With reference to FIGS. 5A and 5B, an embodiment of the device is depicted with the wires 21, 22, 23, 24 of the device 1 selectively deployed such that a point of each wire 21, 22, 23, 24 extended farthest from the tube 10 are each at various distances from the longitudinal axis l of the device 1. For example, the fourth wire 24 may be deployed at a first distance from the longitudinal axis l, the third wire 23 may be deployed at a second distance that is closer to the longitudinal axis l than the first distance, the second wire 22 may be deployed at a third distance that is closer to the longitudinal axis l than the second distance, and the first wire 21 may not be deployed. This setup of the wires 21, 22, 23, 24 may allow for device 1 contact to target tissue of various body lumen anatomies. For example, a circumference defined by the radially outer-most points of the wires 21, 22, 23, 24 in FIG. 5B is an irregular, non-circular shape that may accommodate a non-circular body lumen or a circular body lumen with walls that are folded into a non-circular shape. This setup of the wires 21, 22, 23, 24 may also allow for an off-center orientation of the central lumen 15 within a body lumen. A medical professional may selectively deploy the wires 21, 22, 23, 24 in order to customize the deployment orientation of the device 1. Although this deployment of wires 21, 22, 23, 24 is illustrated in FIGS. 5A and 5B, in some embodiments various deployment distances of the wires 21, 22, 23, 24 radially extended from the longitudinal axis l may be employed as desired by the medical professional for treatment (e.g., as illustrated in FIG. 8, discussed below).

Figure 6A:
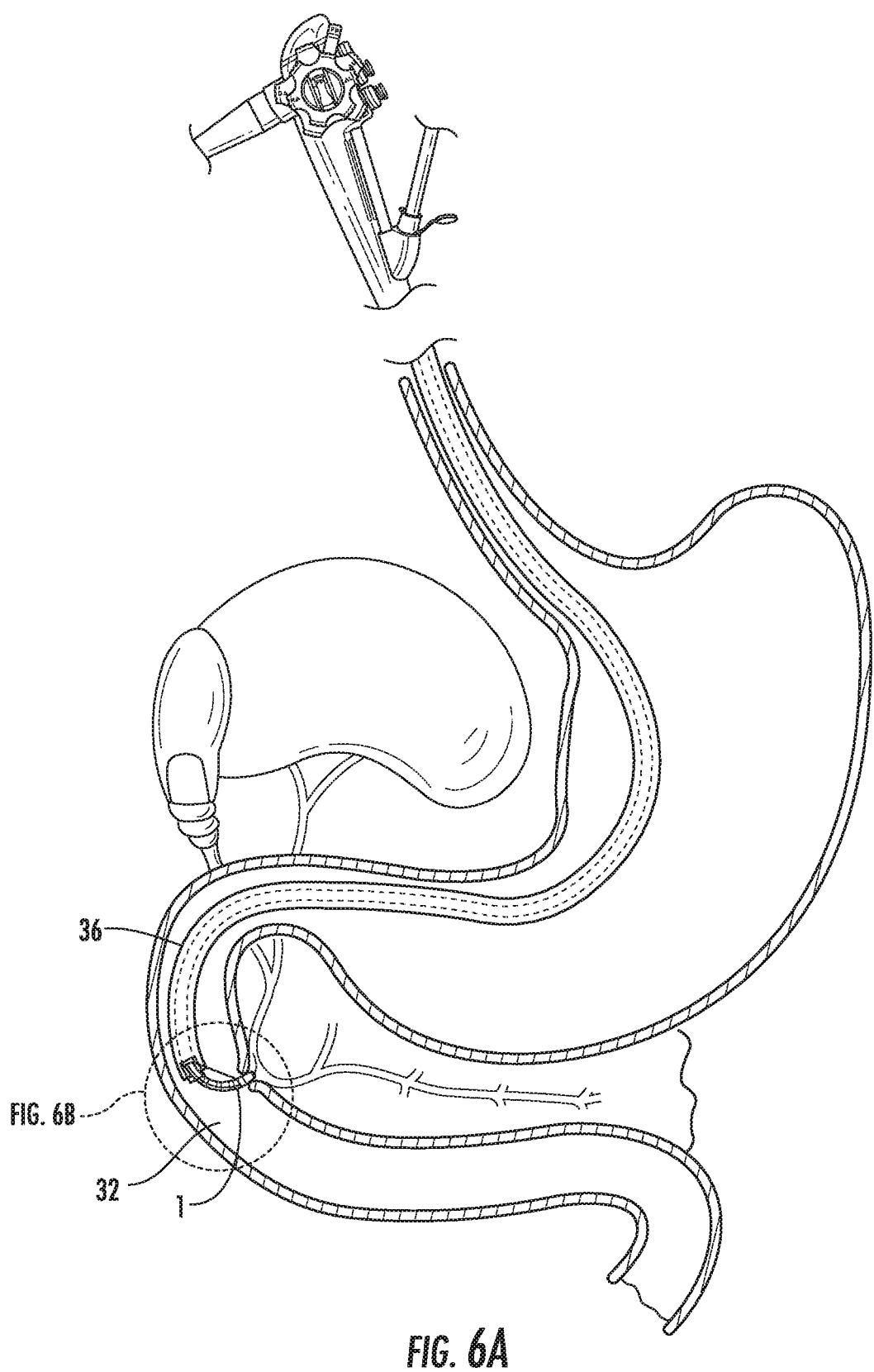
FIG. 6A illustrates a system with the device of FIGS. 1A-5B being used to cannulate a body lumen opening, according to an embodiment of the present disclosure.
Figure 6B:
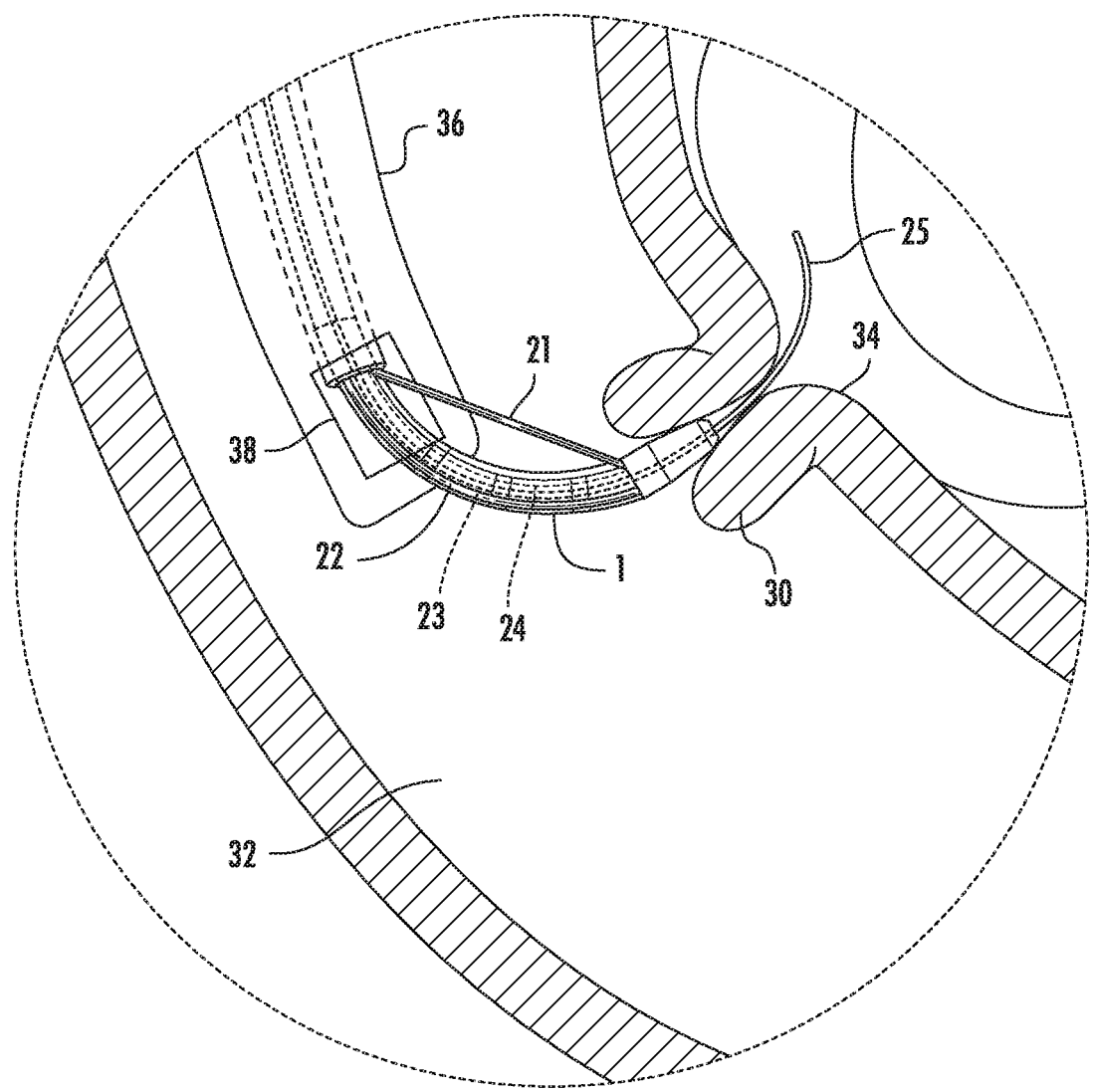
FIG. 6B illustrates a close-up view of the system of FIG. 6A.

With reference to FIGS. 6A and 6B, an embodiment of a system and method for selective cannulation during an ERCP procedure is illustrated, which includes a guidewire 25 and the device 1 being directed into a body lumen opening such as the major papilla 30 (e.g., ampullary entry) near the descending duodenum 32 to access the Sphincter of Oddi Complex 34. A distal portion of an endoscope 36 (e.g., a duodenoscope) may be positioned within the descending duodenum 32. The guidewire 25 and the medical device 1 may be advanced through a working channel of the endoscope 36 towards the major papilla 30. Additionally, the guidewire 25 and/or the medical device 1 may be advanced into the major papilla 30. Accessing the papilla 30 may be difficult because the opening diameter is smaller than the diameter of many medical devices, the opening may be completely collapsed/closed, and/or the opening may extend into the descending duodenum 32 at an angle that may be difficult to visualize and/or access the opening. Thus, a medical professional may articulate the medical device 1 and guidewire 25 by manually rotating the device 1, by using an elevator 38 within the distal end of the endoscope 36, and/or by translating one or more wires 21, 22, 23, 24 proximally to better align or orient the device 1 and/or guidewire 25 with respect to the opening of the papilla 30. A medical professional is able to steer, maneuver, articulate, etc., the distal end of the device 1 by proximally translating one or more wires 21, 22, 23, 24 such that a distal end of the one or more translated wires 21, 22, 23, 24 pulls proximally on the distal end of the device 1, causing the distal end of the device to bend in a direction of the one or more wires 21, 22, 23, 24. A medical professional may steer the distal end of a device 1 such that it is substantially aligned with the major papilla 30 while advancing or subsequently advancing the device 1 and or the guidewire 25 distally into the papilla 30 for cannulation of the opening. As a wire 21 is translated proximally, it may extend out of a wire lumen of the device 1 in a substantially straight configuration (e.g., compared to the arced configurations of the extended wires 21, 22, 23, 24 of FIGS. 1C-5D) when the distal end of the tube bends, e.g., as illustrated in FIG. 6B. A tensional force imposed on a wire 21, 22, 23, 24 by the medical professional may determine the articulation of the wire 21 and/or the device 1. The wire 21 may be brought into contact with the tissue of the papilla 30 before, during, or after cannulation and subsequently energized to cut and enlarge the body lumen. After cannulation, the wires 21, 22, 23, 24 may be further translated by the medical professional to steer further into the anatomy of the patient (e.g., as illustrated in FIG. 8, discussed below). Pulling proximally on one of the wires 21, 22, 23, 24 may steer the device 1 in the direction that the one wire 21, 22, 23, 24 radially extends. Pulling on multiple wires 21, 22, 23, 24 may steer the device in a radial vector direction that is a summation of the multiple wires 21, 22, 23, 24, e.g., the device 1 may be steered by a plurality of wires 21, 22, 23, 24 in a selected direction for positioning relative to a body lumen. Translating one or more wires 21, 22, 23, 24 distally may deploy the translated wire(s) 21, 22, 23, 24 radially away from the device 1 such that the wires 21, 22, 23, 24 push against a tissue and steer the device radially away from the distally translated wires 21, 22, 23, 24. Multiple wires 21, 22, 23, 24 may be translated distally or proximally individually or simultaneously, in various combinations of number of wires, as desired.

Figure 7:
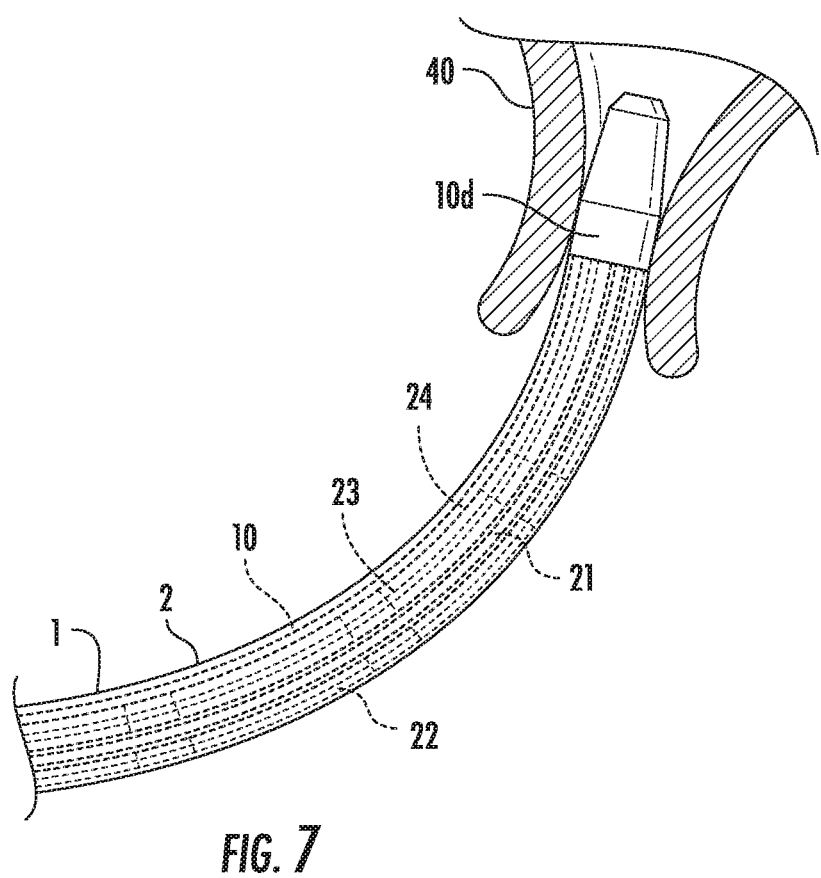
FIG. 7 illustrates the device of FIGS. 1A-6B being articulated toward a body lumen, according to an embodiment of the present disclosure.

With reference to FIG. 7, an embodiment of the device is depicted with the device 1 steered toward and into a body lumen 40 in the closed configuration with the sheath 2 slid distally over the tube 10 and covering the wires 21, 22, 23, 24. In this and other embodiments, the device 1 may also be steered in the open configuration, e.g., as illustrated and discussed with reference to FIGS. 6A and 6B. Steering the device 1 in the closed configuration may be desirable to prevent frictional forces of a working channel of a scope, or a lumen of a catheter, or the patient anatomy from acting on the wires 21, 22, 23, 24. Such friction may dislodge the wires 21, 22, 23, 24 from the wire lumens of the tube 10 and/or cause damage to body tissue. The closed configuration may also prevent an inadvertent energizing of the wires 21, 22, 23, 24 from adversely interacting with surrounding body tissue with the sheath acting as an insulative barrier between the wires 21, 22, 23, 24 and the surrounding anatomy. For example, as shown with reference to FIG. 7, a medical professional may steer the distal end 10*d* of the device 1 in the closed configuration to orient the distal end 10*d* into a position where the wires 21, 22, 23, 24 may be deployed to cannulate the body lumen 40. The device 1 may be steered by translating one or more wires 21, 22, 23, 24 proximally, e.g., such as translating the first wire 21 and the second wire 22 so that the tube 10 and sheath 2 are bent to bring the distal end 10*d* toward and into the body lumen 40. After cannulation, the wires 21, 22, 23, 24 may be further translated by the medical professional to steer further into the anatomy of the patient in the closed configuration or in the open configuration by retracting the sheath 2 proximally.

Figure 8:
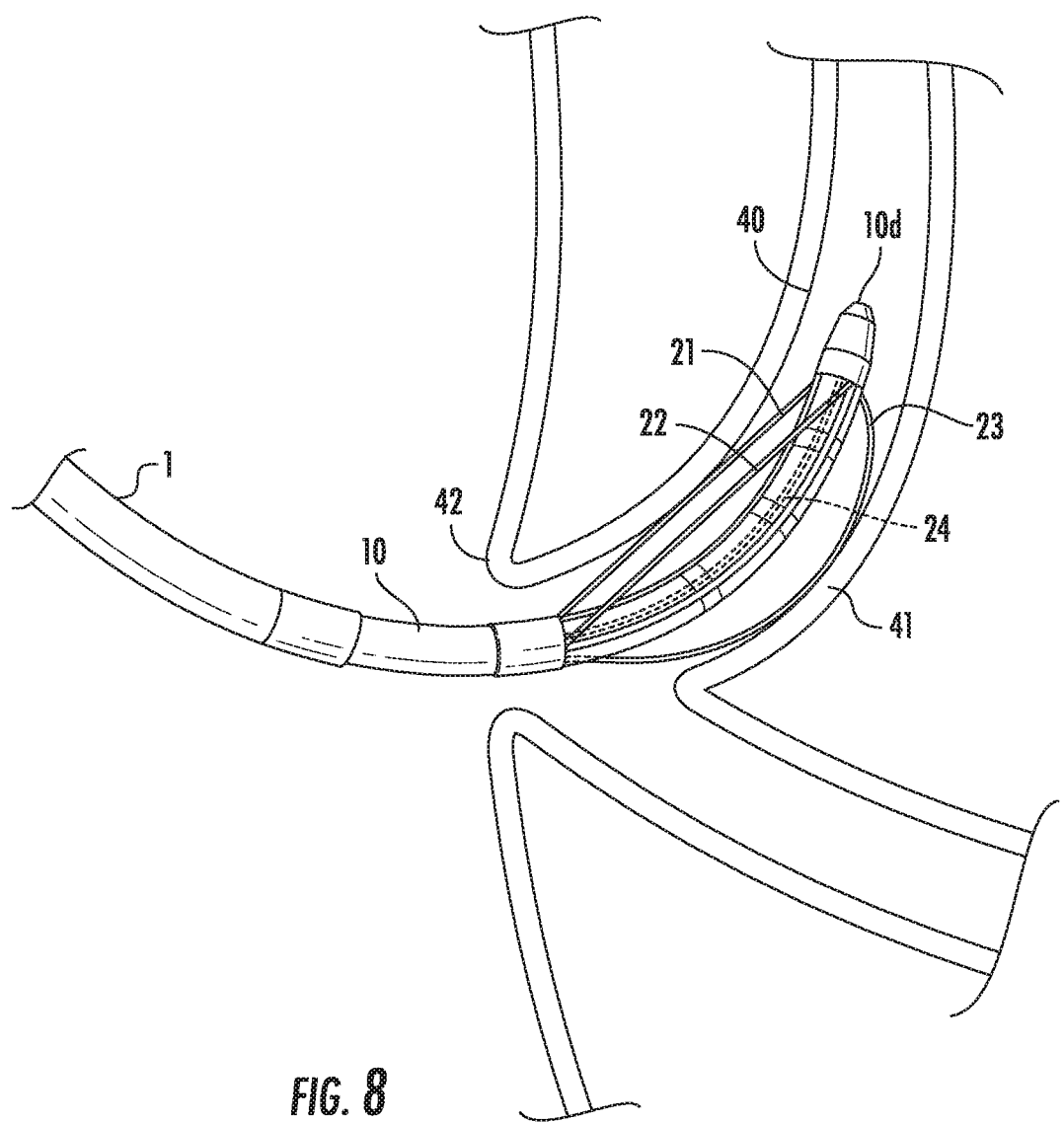
FIG. 8 illustrates the device of FIGS. 1A-7 being used within a body lumen, according to an embodiment of the present disclosure.

With reference to FIG. 8, an embodiment of the device is depicted with a medical professional steering the device 1 into a body lumen 40. The medical professional may translate the tube 10 distally past the opening 42 into the body lumen 40. The tube 10 may be bent while in the body lumen 40 such that the distal end 10*d* and wires 21, 22, 23, 24 are oriented in the body lumen 40 for deployment to the target tissue 41. For example, in FIG. 8, the first wire 21 and second wire 22 may be translated proximally such that the wires 21, 22 pull on the distal end 10*d* and bend the tube 10 to navigate and position the device 1 within the body lumen 40. The third wire 23 may be deployed into contact with the target tissue 41 of the body lumen 40 by the medical professional distally translating the third wire 23. The fourth wire 24 is not manipulated at this point in the procedure as it is not currently being used for articulating the device 1. The third wire 23 may be energized to enlarge the body lumen 40 and/or cut the target tissue 41. Additionally, or alternatively, the first wire 21, second wire 22, and/or fourth wire 24 may be selectively energized to sequentially enlarge the body lumen 40 and/or cut the target tissue 41.

In various embodiments, described here or otherwise within the scope of the present disclosure, a sphincterotomy procedure may be performed by steering an embodiment of a device such that the distal end of the device is against an opening of a body lumen (such as an ampulla). The distal end may be advanced through the body lumen and steered through the lumen and/or toward a desired duct. A guidewire may be advanced through a central lumen of the device. The location and position of portions of the device and/or the guidewire may be observed, e.g., via fluoroscopy. Further steering of the device and/or the guidewire may be performed to achieve cannulation by articulating a distal end of the device into the body lumen. Wires of the device that are coupled to a power source, e.g., a diathermy connection, may be partially deployed, e.g., in the formation of FIG. 1D having four wires deployed about the device. The wires may be partially deployed at a smaller overall diameter than the diameter of the wires when fully deployed. A medical professional may energize one or more of the wires at sequentially increasing diameters of deployment until a desired opening of the body lumen is achieved. Once a larger opening of the body lumen is achieved, the wires may be translated proximally into the undeployed configuration. The device may be removed from the patient, leaving the guidewire in the body lumen to guide another device to be used in the procedure, or the same device used to perform the sphincterotomy may continue to be used for the procedure.

In various embodiments, a flexible elongate tube of a device may comprise an extrusion of multiple lumens. The lumens may be extended through a proximal end of the tube to the distal end of the tube, and a portion of the lumen(s) may be exposed to an external surface of the tube. One or more lumens (e.g., a wire lumen) may terminate at a point that is proximal to the distal end of the tube. The lumens may be configured to accept instruments and/or fluids (e.g., a contrast agent, a wire, a guidewire) of the device through at least a portion of the lumen and may extend out of a lumen where the lumen is exposed to the outer surface of a tube. Such instruments may extend partially along a lumen and may extend external to the lumen along various portions of the lumen exposed to an outer surface of the elongate tube. Such instruments or portions of an instrument extending external to a lumen may break through a wall of the lumen (e.g., through perforations, thin walls, apertures, or the like) and/or tube such that the instrument is external to the lumen at the outer surface of the tube. One or more ends of the tube may be drawn down to a thinner outer diameter (compared to the remainder of the tube) such that a some or all of the wire lumens decrease in inner diameter and taper distally to a closed distal end and/or the tube is treated at the tip such that some of or all of the wire lumens are closed at an end. A drawn-down distal or proximal end may have a smaller diameter than a diameter of other portions of the tube. A portion of a lumen may be a C-shaped channel extending along a portion of the flexible elongate tube, e.g., where a portion of a wire may extend outside of the tube. The channel may comprise other shapes such as, e.g., U-shaped, V-shaped, triangular, boxed, or a combination of these shapes, etc. A channel, such as these channels, may be an open channel or a closed channel. A closed channel may have one or more portions of varying wall thickness, e.g., a thinner wall at a portion of the channel.

In various embodiments, a distal portion and/or a distal end of an elongate flexible tube may be articulated via proximal or distal translation of one or more wires. A proximal translation of a wire may pull the distal end of an elongate flexible tube such that the distal portion of the tube bends toward the translated wire. In the closed configuration with the sheath slid distally over the wires, a distal translation of a wire may push against an internal surface of the sheath and push the distal end of the elongate flexible tube such that the distal portion of the tube bends away from the translated wire. A medical professional may translate two or more wires such that the tube bends towards (e.g., proximal wire translation) or away (e.g., distal wire translation) from a summation of the applied force vectors on the distal portion and/or distal end of the elongate flexible tube. A medical professional may translate one or more wires via a handle at the proximal end of the flexible elongate tube containing a pulley assembly connected to each of the wires that is actuatable to selectively, individually and/or independently translate each of the wires within the respective wire lumens.

In various embodiments, a distal end of a wire may extend to and terminate at an anchor of a flexible elongate tube. The anchor may be a fixed portion of the elongate tube that a wire may be securely attached to and allow for movement of the wire to be translated to the elongate tube. A portion of a wire that is external to the tube may include an insulative layer that is disposed on at least some of the portion of the wire that is external to the tube. For example, a portion of a wire may be partially coated with aluminum oxide, PTFE, or the like. Each wire may be arranged as a monopolar electrode or as a bipolar electrode, and each electrode may be selectively, individually and/or independently energized. One or more wires may be visually marked such that they are differentiated from at least one other wire (e.g., by color, radiopacity, or the like), e.g., to allow a medical professional to locate and keep track of one or more wires during operation. For example, one or more wires of a first color may be conductive while one or more other wires of a second color is not. Also, the medical professional may only want to deploy a selected wire that may uniquely colored for the medical professional to keep track of.

In various embodiments, an elongate flexible tube may comprise polytetrafluoroethylene (PTFE), fluorinated ethylene propylene (FEP), polyether ether ketone (PEEK), or the like, or a combination thereof. The tubes may be extruded to include one or more lumens described herein. An extruded tube may include the one or more lumens extending from a proximal end to the distal end even though a portion or an entirety of each lumen may not contain a wire, an instrument, a fluid, etc. In some embodiments, as mentioned above, the lumens may be configured to be breached by a user (e.g., to deploy an external portion of a wire) through perforations, thin walls, etc., so that, for example, wires are not exposed until a medical professional is about to use the device or so that the device may be stripped from an instrument (such as a guidewire) without needing to proximally translate the entire device off of the instrument.

In various embodiments, the wire lumens within the flexible elongate tube may be arranged in different configurations and combinations depending on the instrument and requirements for a particular application. For example, a lumen configured for a guidewire may also be configured (or instead be configured) for delivery of a contrast agent, etc. Embodiments described and illustrated herein are not meant to exclusively include only those lumens, and do not necessarily need to include all of the lumens illustrated.

The devices, systems, and methods of the present disclosure may be used as sphincterotomes for cannulation, papillotomy, sphincterotomy, and the like. Exemplary devices, systems, and methods with which embodiments of the present disclosure may be implemented include, but are not limited to, those described in U.S. Pat. No. 6,676,659, filed Aug. 14, 2001 and titled, "Steerable Sphincterotome and Methods for Cannulation, Papillotomy and Sphincterotomy," U.S. Pat. No. 6,827,718, filed Dec. 6, 2001 and titled, "Method of and Apparatus for Positioning and Maintaining the Position of Endoscopic Instruments," U.S. Pat.

No. 7,371,237, filed Sep. 2, 2003 and titled, "Steerable Sphincterotome and Methods for Cannulation, Papilotomy and Sphincterotomy," U.S. Pat. No. 7,635,363, filed Nov. 19, 2004 and titled, "Method of and Apparatus for Positioning and Maintaining the Position of Endoscopic Instruments," U.S. Pat. No. 8,231,621, filed Dec. 16, 2009 and titled, "Method of and Apparatus for Positioning and Maintaining the Position of Endoscopic Instruments," U.S. Pat. No. 8,579,895, filed Jul. 30, 2012 and titled "Method of and Apparatus for Positioning and Maintaining the Position of Endoscopic Instruments," U.S. Pat. No. 9,352,124, filed Nov. 12, 2013 and titled "Method of and Apparatus for Positioning and Maintaining the Position of Endoscopic Instruments," U.S. patent application Ser. No. 15/158,052, filed May 18, 2016 and titled "Method of and Apparatus for Positioning and Maintaining the Position of Endoscopic Instruments," and U.S. Provisional Patent Application, 62/787,820, filed Jan. 3, 2019 and titled, "Devices, Systems and Methods for Accessing a Body Lumen" each of which are herein incorporated by reference in their entirety. Exemplary devices or features described therein may be implemented in the embodiments or one or more features of the present disclosure.

In various embodiments, a lumen of the flexible elongate tube may be configured to receive a guidewire such that a distal portion of the guidewire may extend distally beyond the distal end of the elongate tube. The elongate tube may include a flexible distal portion and be configured to move with the translation of a wire (e.g., flex, bend, rotate, wobble, spin, etc.) in a plurality of directions (e.g., x, y, and/or z directions), thereby imparting an identical or similar direction of movement to the distal portion of the guidewire and/or the distal end of a tube. The distal portion of the elongate tube may be configured to move in a linear motion (e.g., moving in a single direction along a straight line relative to a longitudinal axis of the elongate tube), and/or in a reciprocating motion (e.g., backwards and forwards in a straight line along a longitudinal axis of the elongate tube). The distal portion of the elongate tube may be configured to swing from side-to-side in a vibrating or oscillatory motion. The distal portion of the elongate tube may be configured to move in a rotary motion (e.g., 360 degrees of rotation around the longitudinal axis of the elongate tube).

In various embodiments, fluoroscopy may assist in positioning a system or medical device according to the present disclosure, or for confirming the location of lumens, wires, tissues, presence of one or more bodies such as gallstones, etc. A contrast agent may be injected through a central lumen of the medical device and into or about the body lumen for performing fluoroscopy. A guidewire may be withdrawn from the lumen to allow the contrast agent to be injected through the same lumen. Alternatively, a contrast agent may be injected in the lumen containing the guidewire such that the contrast agent flows through the lumen about the guidewire. Alternatively, a lumen or a portion of a multi-lumen tube (e.g., a bifurcated lumen) may be dedicated to the flow of a contrast agent from a medical device. Alternatively, a lumen may be used for a first purpose and later be used for a second purpose, e.g., first to receive a guidewire and second to flow a contrast agent. The contrast agent may comprise iodine, barium sulfate, gadolinium, or the like, or some combination thereof.

In various embodiments, a device may have a safety feature located along a proximal end of the device. The safety feature may only permit energizing of one or more wires when a power activation mechanism, e.g., a foot pedal, a switch, or the like, is fully engaged in addition to the wires being partially or fully deployed, e.g., deployed a certain distance radially away from the longitudinal axis, deployed a certain distally translated distance through a lumen, deployed fully. The safety feature may reduce or eliminate the possibility of the medical professional inadvertently energizing the wires at an undesirable tissue location or at an undesirable moment during the procedure. A safety feature may include a restrictive cover on a handle of a device that may restrict the medical professional to making a diathermy connection only when the cover is retracted from over the connectors (e.g., a connection port) for the conductive wire(s) running from the power source (e.g., generator) to the catheter. In some embodiments, the restrictive cover is part of the sheath. Retraction of the sheath may expose the wires for receiving and delivering energy may also uncover the connectors, allowing for the conductive wires to be connected to the ports and the device energized.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a flexible elongate tube having a proximal end, a distal end, a longitudinal axis extending along a length of the tube, an outer surface, and a distal portion proximal to the distal end that extends longitudinally along a portion of the length of the tube, the distal end configured to access an opening of a body lumen;
   a plurality of wire lumens extending from the distal end of the tube toward the proximal end of the tube, the wire lumens radially offset from and substantially parallel with the longitudinal axis, wherein at least a portion of each of the plurality of wire lumens is in the form of a longitudinal open channel having a length that extends along a length of the distal portion and is radially exposed to the outer surface along the length of the distal portion;
   a central lumen extending from the distal end of the tube toward the proximal end of the tube;
   a plurality of wires, each wire substantially flush with the outer surface of the flexible elongate tube along the length of the distal portion, and a portion of each wire extendable radially externally to the respective wire lumen along the portion of the wire lumen that is radially exposed to the outer surface; and
   a sheath slidable about the flexible elongate tube between a closed configuration in which the sheath is positioned distally such that the longitudinal open channel of each of the plurality of wires is covered by the sheath and an open configuration in which the sheath is positioned proximally such that the longitudinal open channel of each of the plurality of wires is not covered by the sheath;
   wherein the plurality of wires is configured to bend the distal end of the flexible elongate tube by proximally translating one or more of the plurality of wires such that a distal end of the one or more translated wires pulls proximally on the distal end of the flexible elongate tube, causing the distal end of the flexible elongate tube to bend in a direction of the one or more wires.

2. The medical device of claim 1, further comprising a shoulder disposed on the distal end of the flexible elongate tube, the shoulder having an outer diameter that is wider than an inner diameter of the sheath such that such that the sheath cannot be extended distally past the shoulder.

3. The medical device of claim 1, wherein at least one of the plurality of wires is electrically conductive and configured to be coupled to a power source.

4. The medical device of claim 1, wherein each of the plurality of wires is individually transitionable between an undeployed configuration substantially within the respective wire lumen, and a deployed configuration with a portion of the wire extended radially away from the respective wire lumen.

5. The medical device of claim 1, further comprising a handle at the proximal end of the flexible elongate tube, the handle comprising a pulley assembly connected to each of the plurality of wires, wherein the handle is actuatable to individually translate the wires within the respective wire lumens.

6. The medical device of claim 1, wherein each of the plurality of wire lumens are arranged circumferentially about the longitudinal axis.

7. The medical device of claim 1, wherein each of the plurality of wires is visually marked such that they are differentiated from at least one other wire of the plurality of wires.

8. A medical device, comprising:
a flexible elongate tube having a proximal end, a distal end, a longitudinal axis extending along a length of the tube, an outer surface, and a distal portion proximal to the distal end that extends longitudinally along a portion of the length of the tube, the distal end configured to access an opening of a body lumen;
a plurality of marker bands configured to visually indicate a location and orientation of the device, the plurality of marker bands comprising a distal marker band disposed about the flexible elongate tube at the distal end;
a plurality of wire lumens extending from the distal end of the tube toward the proximal end of the tube, the wire lumens radially offset from and substantially parallel with the longitudinal axis, wherein at least a portion of each of the plurality of wire lumens is in the form of a longitudinal open channel having a length that extends along a length of the distal portion and is radially open along the length of the outer surface along the distal portion;
a central lumen extending from the distal end toward the proximal end of the tube; and
a plurality of wires, each wire extending along a respective wire lumen, each wire substantially flush with the outer surface of the flexible elongate tube along the length of the distal portion, and a portion of each wire configured to extend radially externally to the respective wire lumen along the portion of the wire lumen that is radially open along the outer surface;
wherein the plurality of wires is configured to bend the distal end of the flexible elongate tube by proximally translating one or more of the plurality of wires such that a distal end of the one or more translated wires pulls proximally on the distal end of the flexible elongate tube, causing the distal end of the flexible elongate tube to bend in a direction of the one or more wires.

9. The medical device of claim 8, further comprising a sheath that is slidable about the flexible elongate tube between a closed configuration in which the sheath is positioned distally such that the longitudinal open channel of each of the plurality of wires is covered by the sheath and an open configuration in which the sheath is positioned proximally such that the longitudinal open channel of each of the plurality of wires is not covered by the sheath, the plurality of marker bands comprising a sheath marker band disposed about the sheath at a distal end of the sheath, and wherein the distal marker band and the sheath marker band are visually marked such that they are differentiated from each other.

10. The medical device of claim 9, wherein the sheath band distally tapers from a larger diameter to a smaller diameter.

11. The medical device of claim 9, wherein the plurality of marker bands further comprise a marker band disposed about the flexible elongate tube at a position proximal to the distal portion and a marker band disposed about the flexible elongate tube within the distal portion.

12. The medical device of claim 8, further comprising a handle at the proximal end of the flexible elongate tube, the handle comprising a pulley assembly connected to each of the plurality of wires, wherein the handle is actuatable to independently slide each of the plurality of wires within the respective wire lumens.

13. The medical device of claim 8, further comprising a handle at the proximal end of the flexible elongate tube, the handle comprising a pulley assembly connected to each of the plurality of wires, wherein the handle is actuatable to selectively slide each of the plurality of wires within the respective wire lumens.

14. The medical device of claim 8, wherein the plurality of marker bands further comprise a marker band disposed about the flexible elongate tube at a position proximal to the distal portion and a plurality of marker bands disposed about the flexible elongate tube within the distal portion.

15. The medical device of claim 8, wherein the plurality of marker bands are radiopaque.

16. The medical device of claim 15, wherein the plurality of marker bands further comprise a marker band disposed about the flexible elongate tube at a position proximal to the distal portion and a plurality of marker bands disposed about the flexible elongate tube within the distal portion.

17. A method of accessing an opening of a body lumen, comprising:
inserting a flexible elongate tube of a medical device having a distal end into a patient to the opening of the body lumen;
articulating the distal end of the elongate tube toward the opening of the body lumen via at least one of a plurality of conductive wires extending within respective wire lumens through the flexible elongate tube, wherein at least a portion of each of the respective wire lumens is in the form of a longitudinal open channel that extends along a length of the elongate tube and is radially exposed along an outer surface of the elongate tube, the plurality of conductive wires connected at the distal end of the tube, each conductive wire substantially flush with the outer surface of the flexible elongate tube along a length of the distal portion and each conductive wire having a distal portion extendable radially from the respective wire lumen external to the outer surface of the elongate tube;

extending a first conductive wire of the plurality of conductive wires radially outward to a first radial distance from the elongate tube into contact with the body lumen; and energizing at least one of the plurality of conductive wires;

wherein the plurality of conductive wires is configured to bend the distal end of the flexible elongate tube by proximally translating one or more of the plurality of conductive wires such that a distal end of the one or more translated conductive wires pulls proximally on the distal end of the flexible elongate tube, causing the distal end of the flexible elongate tube to bend in a direction of the one or more conductive wires.

18. The method of claim 17, further comprising:

cannulating the opening of the body lumen with the distal end of the elongate tube; and extending a second conductive wire of the plurality of conductive wires radially outward to a second radial distance from the elongate tube into contact with the body lumen.

19. The method of claim 17, further comprising retracting a sheath from about the flexible elongate tube after cannulating the opening of the body lumen.

20. The method of claim 17, wherein the device further comprises a sheath, wherein the flexible elongate tube is inserted with the sheath in a closed configuration in which the sheath is positioned such that the longitudinal open channel of each of the plurality of wires is covered by the sheath, and wherein upon positioning the device at the opening of the body lumen, the sheath is repositioned to an open configuration wherein the longitudinal open channel of each of the plurality of wires is not covered by the sheath.

* * * * *